United States Patent [19]

Yaginuma et al.

[11] Patent Number: 5,379,329
[45] Date of Patent: Jan. 3, 1995

[54] METHOD AND APPARATUS FOR INSPECTING END FACE OF PELLET

[75] Inventors: Yoshitaka Yaginuma, Naka; Yoshihiro Inoue, Tokyo, both of Japan

[73] Assignees: Mitsubishi Nuclear Fuel Co.; Mitsubishi Materials Corporation, both of Tokyo, Japan

[21] Appl. No.: 202,169

[22] Filed: Feb. 25, 1994

[30] Foreign Application Priority Data

Feb. 25, 1993 [JP] Japan .................................. 5-037109

[51] Int. Cl.⁵ .............................................. G21C 17/00
[52] U.S. Cl. ..................................... 376/248; 209/585; 356/237
[58] Field of Search ............... 376/245, 248, 261; 209/525, 526, 529, 538, 577, 585, 587; 356/237, 385; 53/504

[56] References Cited

U.S. PATENT DOCUMENTS

| | | | |
|---|---|---|---|
| 4,377,238 | 3/1983 | Wilks et al. | 376/248 |
| 4,532,723 | 8/1985 | Kellie et al. | 376/248 |
| 4,969,746 | 11/1990 | McConnell et al. | |
| 5,303,277 | 4/1994 | Yaginuma | 376/261 |
| 5,309,486 | 5/1994 | Lichauer et al. | 376/248 |

FOREIGN PATENT DOCUMENTS 3309584 10/1983 Germany .

OTHER PUBLICATIONS

Database WPI, Derwent Publications, AN 87-323587 & JP4-A-62-229053, Oct. 7, 1987.
Database WPI, Derwent Publications, AN 87-323588 & JP-A-62-229054, Oct. 7, 1987.
Database WPI, Derwent Publications, AN 89-197287 & JP-A-136053, May 29, 1989.

Primary Examiner—Daniel D. Wasil
Attorney, Agent, or Firm—Oblon, Spivak, McClelland, Maier & Neustadt

[57] ABSTRACT

In a method for inspecting a dished end face of a nuclear fuel pellet, a focused beam of light is emitted to a dish of the end face of the nuclear fuel pellet while a parallel beam of light is being emitted to the end face thereof. An image of the end face of the nuclear fuel pellet is picked up and the quality of the pellet is judged based on the picked-up image. An apparatus for inspecting a dished end face of a nuclear fuel pellet is also disclosed. The inspection apparatus includes a handling unit for holding the pellet during inspection, a lighting unit for lighting the end face of the pellet, an image pick-up unit disposed adjacent to the handling unit for picking up image data as to the end face of the pellet, and a judging unit operably connected to the image pick-up unit for analyzing the image data outputted from the image pick-up unit to judge quality of the nuclear fuel pellet. The lighting unit includes emitting optical systems for emitting a focused beam of light to a dish of the end face of the pellet while emitting a parallel beam of light to the entire end face of the pellet.

5 Claims, 4 Drawing Sheets

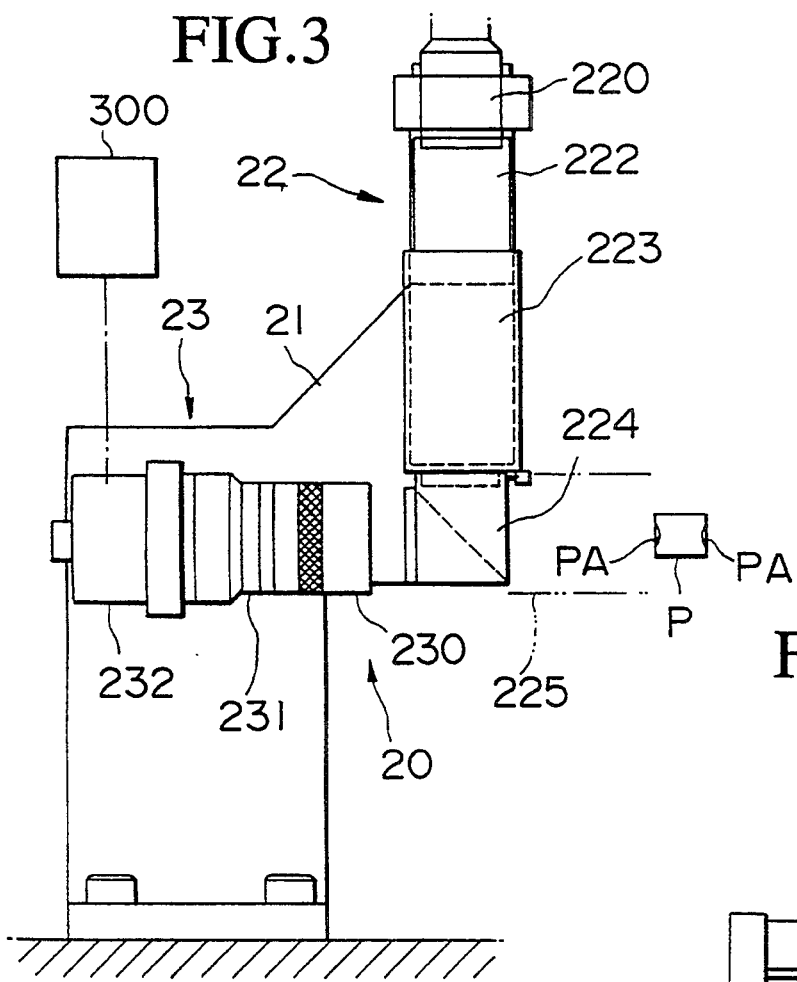
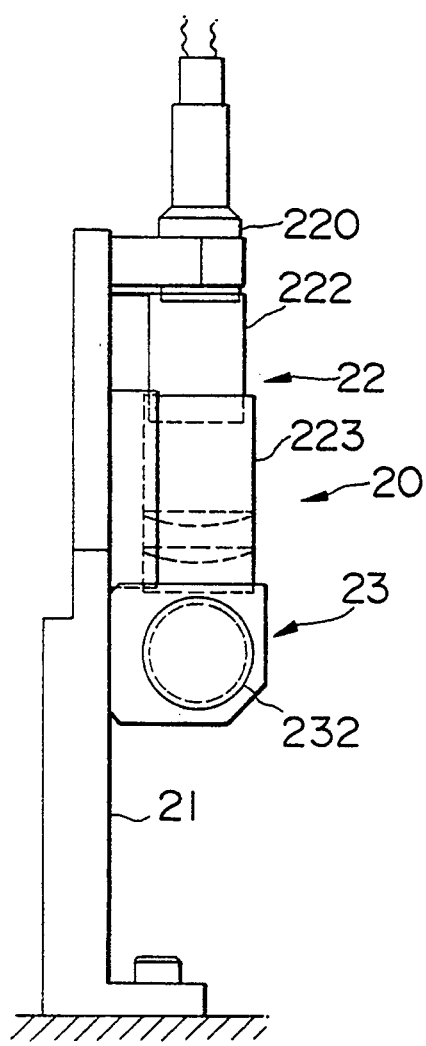
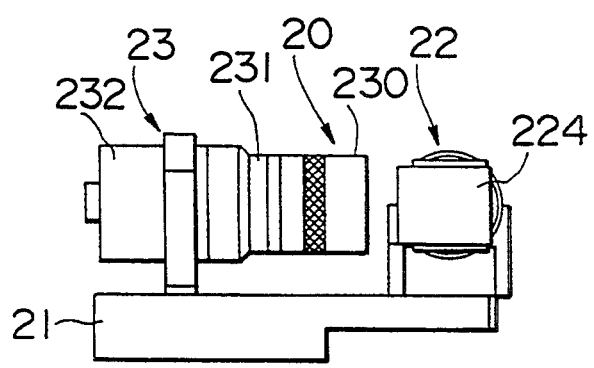

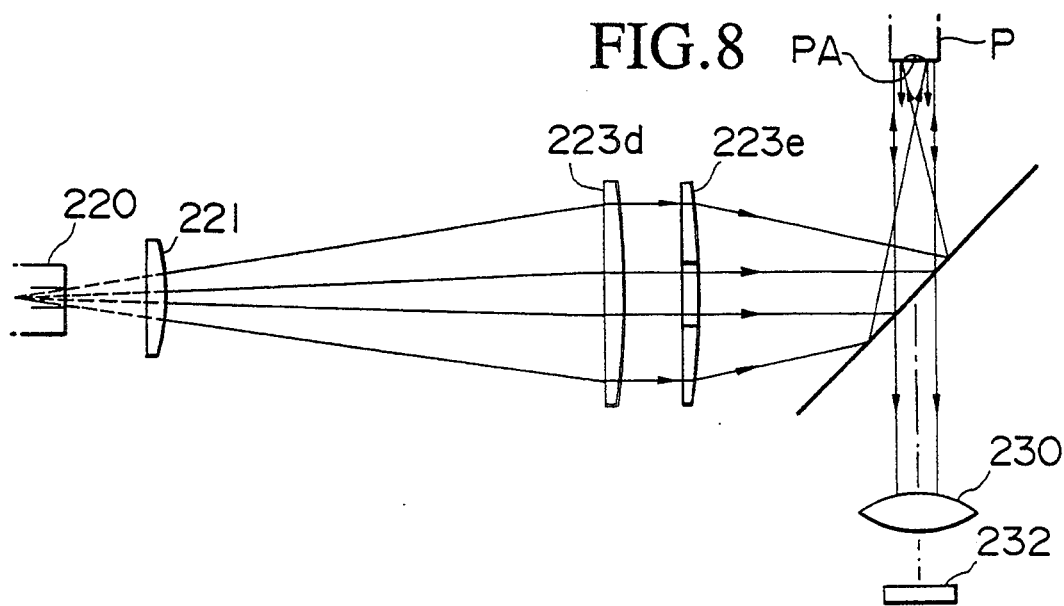
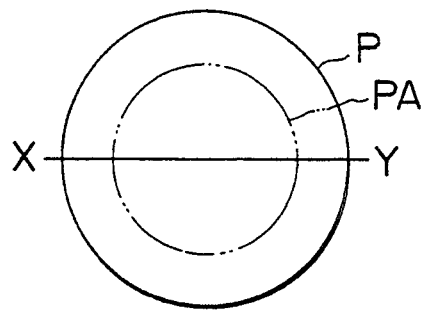
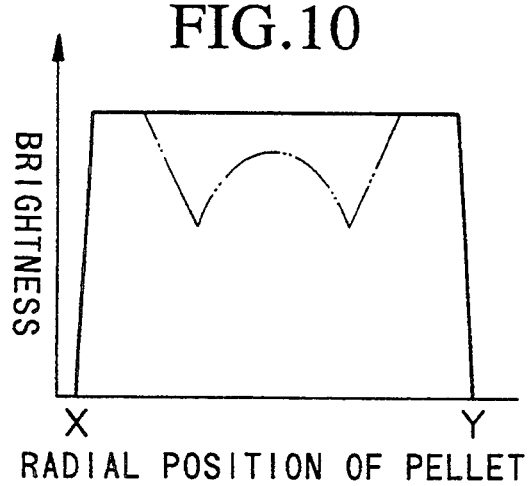
RADIAL POSITION OF PELLET

METHOD AND APPARATUS FOR INSPECTING END FACE OF PELLET

BACKGROUND OF THE INVENTION

The present invention relates to a method and apparatus for inspecting an end face of a nuclear fuel pellet at the center of which a spherical dish or recess is formed, and in particular to a method and apparatus of a type which picks up an image of the pellet end face and judges the quality of the pellet based on this image.

When an image of a pellet end face with a spherical dish is picked up by emission of a parallel beam of light to the pellet end face, the image obtained will have a dark portion around the dish. Therefore, when the obtained image is processed into a binary image, It is difficult to distinguish the dish from defects such as chipping.

Japanese Patent Application, First (A) Publication No. 1136053, describes a method which circumvents the aforesaid problem by adding correction data from a standard image upon processing of the picked-up image into a binary image. This method is, indeed, effective on the assumption that images of the specimens are picked up in a manner similar to the standard image. However, this assumption is often not applicable in practice. In addition, due to the undue load on image processing, inspection is time-consuming, so that high speed inspection of pellet end faces has not been attained.

SUMMARY OF THE INVENTION

It is therefore the object of the present invention to provide a method and apparatus for inspecting an end face of a pellet by which the pellet end face can be inspected smoothly and certainly, and by which load on tile image processing can be substantially reduced to ensure automatic inspection at high speed.

According to a first aspect of the present invention, there is provided a method for inspecting a dished end face of a nuclear fuel pellet, comprising the steps of:
emitting a focused beam of light to a dish of the end face of the nuclear fuel pellet while emitting a parallel beam of light to the entire end face thereof; and
picking-up an image of the end face of the nuclear fuel pellet and judging quality of the pellet based on the picked-up image.

In the foregoing method, it is preferable that the parallel beam of light and the focused beam of light be produced from a common light source.

According to another aspect of the invention, there is provided an apparatus for inspecting a dished end face of a nuclear fuel pellet, comprising:
a handling unit for holding the pellet during inspection;
a lighting unit for lighting the end face of the pellet, the lighting unit including a first means for focusing a parallel beam of light onto the entire end face of the pellet and a second means for sending a focused beam of light to a dish of the end face of the pellet;
an image pick-up unit disposed adjacent to the handling unit for picking up image data as to the end face of the pellet; and
a judging unit operably connected to the image pick-up unit for analyzing the image data outputted from the image pick-up unit to judge quality of the pellet.

In the foregoing apparatus, the lighting unit may include a common light source for emitting a beam of light, and the first means may include a first lens for producing the parallel beam of light from the beam of light emitted from the light source. The second means of the lighting unit may include a second lens having an aperture and focusing the parallel beam of light emitted from the first lens onto the dish of the end face of the pellet while permitting the parallel beam of light to pass through the aperture to the entire end face of the pellet. The first lens may be defined by a piano-convex lens arranged with a plane side thereof directed to the light source and a convex side thereof directed to the pellet.

Furthermore, the handling unit may include a rotary disc for holding a plurality of the nuclear fuel pellets in a line, and a sorting unit attached to the rotary disc for separating defective pellets from non-defective pellets.

BRIEF DESCRIPTION OF THE DRAWINGS

FIG. 3 is a front elevational view of one of the inspection assemblies of FIG. 2;

FIG. 4 is a side elevational view of the inspection assembly of FIG. 3;

FIG. 5 is a bottom view of the inspection assembly of FIG. 3;

FIG. 8 is a schematic view of an optical system used in the inspection assembly of FIG. 2;

FIG. 9 is a schematic view showing an end face of a nuclear fuel pellet; and

FIG. 10 is a diagrammatical representation showing brightness obtained along a line X-Y in FIG. 9.

DETAILED DESCRIPTION OF PREFERRED EMBODIMENTS OF THE INVENTION

An inspection apparatus for end faces of nuclear fuel pellets, in accordance with a preferred embodiment of the present invention, will be described with reference to FIGS. 1 to 10.

Figure 1:
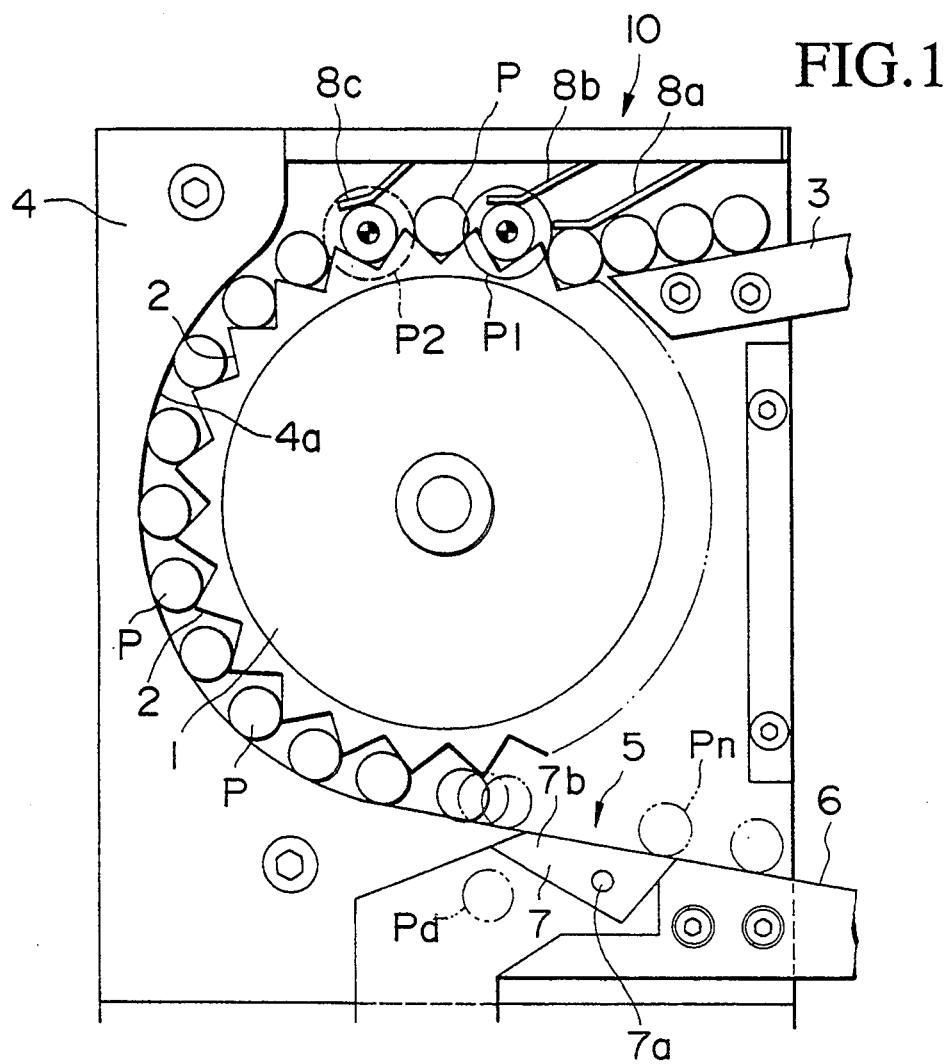
FIG. 1 is a side elevational view of a handling unit of an inspection apparatus in accordance with the present invention.
Figure 2:
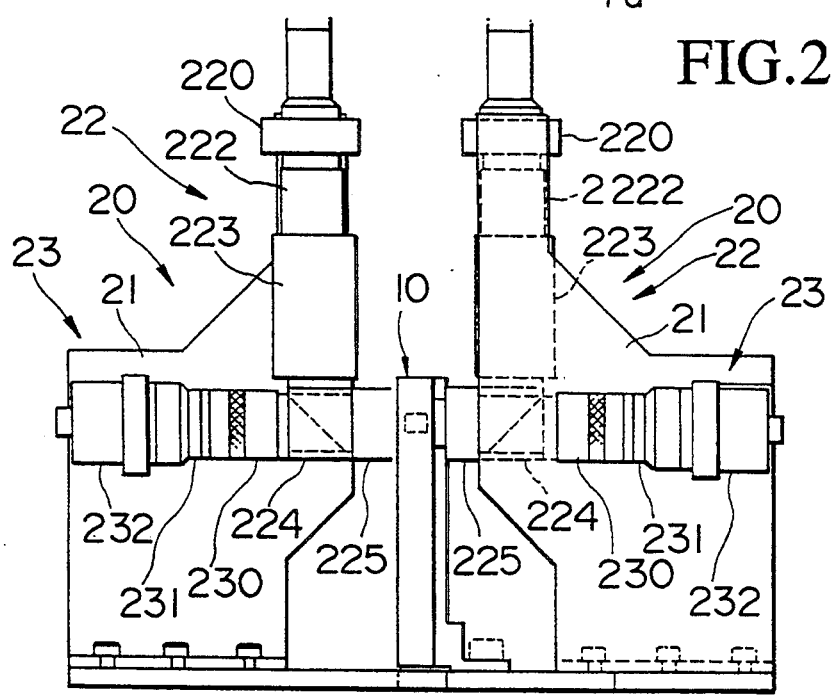
FIG. 2 is a front elevational view showing a pair of inspection assemblies of the inspection apparatus of the invention.

FIG. 1 depicts a pellet-handling unit 10 of the inspection apparatus. The handling unit 10 includes a rotary disc 1 vertically arranged for rotation about a horizontal axis, a loading chute 3 arranged at an upper position adjacent to the rotary disc 1, a guide frame 4 disposed adjacent to the rotary disc 1, a sorting device 5 disposed below the rotary disc 1, and a discharge chute 6. The rotary disc 1 has a plurality of V-shaped grooves or recesses 2 formed in a circumferential surface thereof for receiving nuclear fuel pellets P to be inspected. The loading chute 3 is constructed to successively introduce pellets P into the V-shaped grooves 2 of the rotary disc 1. The guide frame 4, which has an arcuately shaped guide surface 4a directed inwardly, is arranged adjacent to the rotary disc 1 such that the guide surface 4a extends along and covers about half the outer circumference of the rotary disc 1, whereby the pellets P received in the V-shaped grooves 2 are prevented from falling therefrom during rotation of the rotary disc 1. The discharging chute 6 is arranged below the rotary disc 1 so as to be adjacent to the terminal end of the guide surface 4 such that a receiving surface thereof is inclined and flush with the terminal end portion of the guide surface 4. In addition, the sorting device 5 includes a sorting member 7 disposed between the terminal end of the guide surface 4 and the discharge chute 6 so as to be pivotable about an axis 7a, whereby the defective pellets Pd are discharged downwards when the sorting member 7 is pivoted counterclockwise in FIG. 1 such that a forward end 7b thereof is inclined downwards, whereas the non-defective pellets Pn are conveyed to the discharge chute 6 when the sorting member 7 is pivoted clockwise to its original position. Furthermore, a first guide arm or guide member 8a is arranged above the rotary disc i to ensure smooth loading of the nuclear fuel pellet P, whereas second and third guide arms or guide members 8b and 8c are arranged at prescribed positions P1 and P2 above the rotary disc 1. Each guide arm is pivotable or resiliently movable in a vertical direction on so as to be pressed and urged against the pellets P situated in the positions P1 and P2, the positions P1 and P2 being determined so as to correspond to the inspecting positions for both end faces of the pellet, respectively.

Figures 6, 7:
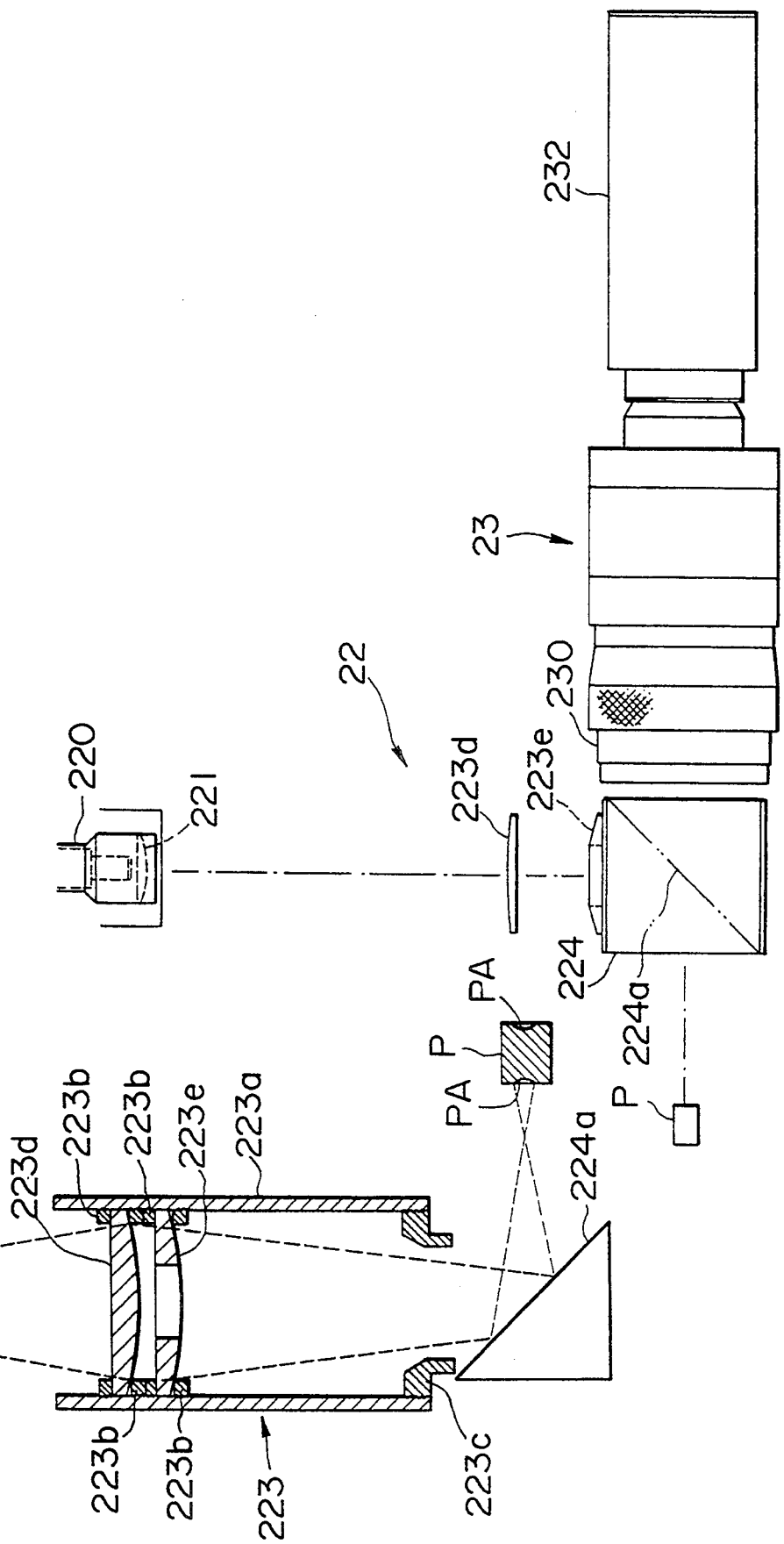
FIG. 6 is a view for explaining a lighting unit of the inspection assembly of the invention.
FIG. 7 is a cross-sectional view of the lighting unit.

A pair of inspection assemblies 20 are provided at opposite sides of the aforesaid handling unit 10, respectively. As best shown in FIG. 3, each inspection assembly 20 comprises a mounting frame 21, a lighting unit 22 for lighting the end face of the pellet situated at a respective inspection position P1 or P2, an image pick-up unit 23 mounted on the mounting frame 21, and a known image processing unit 300 (judging unit) connected to the image pick-up means 23. The lighting unit 22 includes a fiber light source 220, a vertically arranged casing 223 of a cylindrical shape connected to the light source 220 through a hood 222, a half mirror box 224 arranged at the lower end of the casing 223 and directed to the nuclear fuel pellet P through a hood 225. As schematically shown in FIG. 6 or FIG. 8, a light source lens 221 is provided adjacent to the fiber light source 220. As shown in FIG. 7, the cylindrical casing 223 is provided with an internally threaded upper portion, and a plano-convex lens 223d as well as an apertured lens 223e are accommodated and held by each pair of upper and lower screws 223b threadedly engaged with the threaded upper portion of the casing 223. The plano-convex lens 223d is disposed at an upper side adjacent to the light source 220, whereas the apertured lens 228e is arranged below the plano-convex lens 228d with its plane side directed to the light source 220 and with its convex side operatively directed to the pellet end face. In addition, the cylindrical casing 228 is further provided with an internally threaded lower end, on which a tubular member 223c is threaded. Accommodated in the half mirror box 224 is a half mirror 224a which is inclined 45 degrees with respect to an optical axis of a beam of light emitted from the light source 220.

Furthermore, as best shown in FIG. 6, the image pick-up unit 23 is arranged adjacent to the half mirror box 224 such that the half mirror box 224 is situated between the pellet P and the image pick-up unit. The unit 23 comprises a suitable CCD camera 232 and a camera lens 230 attached thereto with an intermediate ring 231 interposed therebetween.

When inspecting the nuclear pellets P using the inspection apparatus as described above, the pellets P are conveyed into the V-shaped grooves 2 of the rotary disc 1 which is intermittently being rotated. As the pellet P received in the V-shaped groove 2 of the rotary disc 1 arrives at the inspection positions P1 or P2, the images of both end faces of the pellet P are successively picked up by the inspection assemblies 20.

More specifically, a beam of light emitted from the fiber light source 220 passes through the light source lens 221 which focuses the beam of light on the plano-convex lens 223d to generate a parallel beam of light, which passes through the aperture of the apertured lens 223e and is reflected by the half mirror 224a onto the end face of the nuclear fuel pellet P situated in each inspection position P1 or P2. Thus, the entire end face of the pellet is lighted by this parallel beam of light. Furthermore, the beam of light which passes through the peripheral portion of the apertured lens 223e is reflected by the half mirror 224a and focused onto the central dish PA formed in the pellet end face. As shown by the two-dot and dash line in FIG. 10, the brightness of the end face is not uniform if only a parallel beam of light is emitted. However, in the present invention, since the focused beam of light is combined with the parallel beam of light, the brightness of the central dish PA of the pellet end face can be made uniform and equal to that of the peripheral portion thereof as shown by solid line in FIG. 10.

In the foregoing situation, the image of the end face of the pellet P is picked up by the CCD camera 232, and the resulting image data is processed and analyzed by the image processing unit, and the quality of the pellet is judged based on the processed image data to determine whether the pellet inspected is defective or non-defective. The pellets Pn judged non-defective are discharged by the discharging chute 6 through the sorting device 5, whereas the pellets Pd judged defective are discharged by the pivoting member 7 of the sorting device 5 downwards.

As described above, in the present invention, the end face of the nuclear fuel pellet is lighted by a parallel beam of light whereas the central dish of the end face is further lighted by a focused beam of light. Therefore, the brightness of the dish of the end face of the pellet can be made uniform and equal to that of the peripheral flat portion thereof. Accordingly, the pellet end face can be inspected smoothly and certainly, and load on the image processing can be substantially reduced to ensure automatic inspection at high speed.

Obviously, many modifications and variations of the present invention are possible in the light of the above teachings. It is therefore to be understood that within the scope of the appended claims, the invention may be practiced otherwise than as specifically described.

Finally, the present application claims the priority of Japanese Patent Application No. 5-37109, filed Feb. 25, 1993, which is herein incorporated by reference.

What is claimed is:

1. A method for inspecting a dished end face of a nuclear fuel pellet, comprising the steps of:
    emitting a focused beam of light to a dish of said end face of said nuclear fuel pellet while emitting a parallel beam of light to the entire end face thereof; and
    picking-up an image of said end face of the nuclear fuel pellet and judging quality of the pellet based on the picked-up image.

2. An inspection method as defined in claim 1, wherein said emitting step comprises producing said parallel beam of light and said focused beam of light from a common light source.

3. An apparatus for inspecting a dished end face of a nuclear fuel pellet, comprising:
- a handling unit for holding said pellet during inspection;
- a lighting unit for lighting said end face of said pellet, said lighting unit including a first means for focusing a parallel beam of light onto the entire end face of said pellet and a second means for sending a focused beam of light to a dish of the end face of said pellet;
- an image pick-up unit disposed adjacent to said handling unit for picking up image data as to the end face of said pellet; and
- a judging unit operably connected to said image pick-up unit for analyzing said image data outputted from said image-pick-up unit to judge quality of said pellet.

4. An inspection apparatus as defined in claim 3, wherein said lighting unit includes a common light source for emitting a beam of light, and wherein said first means of said lighting unit includes a first lens for producing said parallel beam of light from said beam of light emitted from said light source, said second means of said lighting unit including a second lens having an aperture and focusing said parallel beam of light emitted from said first lens onto the dish of the end face of the pellet while permitting said parallel beam of light to pass through said aperture to the entire end face of said pellet.

5. An inspecting apparatus as defined in claim 4, wherein said handling unit includes a rotary disc vertically arranged for rotation about a horizontal axis thereof for holding a plurality of said nuclear fuel pellets in a line, and a sorting unit attached to said rotary disc for separating defective pellets from non-defective pellets.

* * * * *